United States Patent [19]

Morgan et al.

[11] Patent Number: 5,484,285
[45] Date of Patent: Jan. 16, 1996

[54] OVERDENTURE BAR APPARATUS AND METHOD FOR INSTALLING SAME

[76] Inventors: Vincent J. Morgan, 23 Bowditch Rd., Boston, Mass. 02136; Norman J. Shepherd, 26 River Rd., Merrimack, Mass. 01860

[21] Appl. No.: 261,065

[22] Filed: Jun. 16, 1994

[51] Int. Cl.⁶ .............................. A61C 8/00; A61C 13/12; A61C 19/04; A61C 3/02
[52] U.S. Cl. ........................... 433/173; 433/172; 433/72; 433/76
[58] Field of Search ..................... 433/172, 173, 433/174, 175, 176, 72, 75, 76

[56] References Cited

U.S. PATENT DOCUMENTS

| | | | |
|---|---|---|---|
| 3,508,334 | 4/1970 | Weissman | 433/76 |
| 3,576,074 | 4/1971 | Gault | 433/175 |
| 3,919,772 | 11/1975 | Lenczycki | 433/173 |
| 4,283,176 | 8/1981 | Vajda | 433/173 |
| 4,738,623 | 4/1988 | Driskell | 433/173 |
| 4,832,601 | 5/1989 | Linden | 433/173 |
| 4,976,739 | 12/1990 | Duthie, Jr. | 433/174 X |
| 5,219,286 | 6/1993 | Hader | 433/172 |
| 5,320,529 | 6/1994 | Pompa | 433/76 |
| 5,376,004 | 12/1994 | Mena | 433/173 |

*Primary Examiner*—Nicholas D. Lucchesi

[57] ABSTRACT

An overdenture bar assembly is shown having first and second root members each mounting a bar attachment abutment. Each bar attachment abutment has a post formed with a locking taper receivable in a matching tapered bore in the repective root member and a transversely extending bore in a head portion which receives an end of a cylindrical bar. A jig member is shown formed of a flat plate having a central reference bore between two outer bores and an annular insert is closely receivable in each outer bore. The outer bores serve to guide a drill bit to provide parallelism and the top surface of the plate cooperates with a mark on a drill bit to provide a reference for measuring the depth of the bore being formed.

15 Claims, 2 Drawing Sheets

5,484,285

1

OVERDENTURE BAR APPARATUS AND METHOD FOR INSTALLING SAME

BACKGROUND OF INVENTION

This invention relates generally to restorative dentistry and more particularly to bar overdenture systems.

Implant prosthetic systems include a variety of restorations, such as single tooth, partially edentulous and edentulous. One type of prosthetic system employs the use of a bar overdenture. This system comprises a conventional acrylic denture retained by suitable attachments such as clips or the like to an implant supported cast bar. A conventional procedure for implanting the support structure involves a number of office visits as well as laboratory participation. For example, once root implants have been placed in the alveolar ridge and sufficiently healed, threaded healing abutments are removed and appropriate abutments are inserted and tightened with a special torque wrench. Impression posts are inserted with a friction drive wrench and an impression is made from suitable material such as polyvinylsiloxane for transferring abutment locations to a laboratory model or analog. The impression posts are then removed and threaded onto the abutment analog. The analog is then inserted into the impression and a model is poured in the laboratory. The model is then separated from the impression and impression posts are removed with a friction drive wrench. Bar copings are then placed over the analog in the model and secured with special coping screws. A connecting bar is waxed between bar copings, sprues are attached, coping screws removed, the model is invested and cast. The casting is then tried in the model and adjustments made including a new impression if necessary. A passive and precise fit is essential to avoid subsequent implant failure. Polishing caps and metal finishing are completed and the casting is returned to the restorative dentist to try intraorally to confirm a passive fit. Finally the bar is seated over the abutments and tightened thereto with a torque wrench. The denture is then seated over the bar.

SUMMARY OF THE INVENTION

It is an object of the present invention to provide a bar overdenture system which requires fewer procedural steps and less laboratory involvement than is required in conventional systems. Another object of the invention is the provision of a bar overdenture system which is inexpensive yet which is long lasting and provides improved support with essentially no misalignment stresses.

Briefly, in accordance with the invention, first and second root implant members, each having a bore with a selected locking taper formed in its crestal end face, are implanted in a respective socket formed in a patient's alveolar ridge. The root members are positioned using a jig to ensure that the longitudinal axes of the two sockets are parallel with one another as well as being of uniform depth. A healing plug is inserted in each root implant member bore and the implant member is packed with autogenous material and the mucoperiosteal flaps are sutured and allowed to heal. After sufficient healing has taken place, e.g. three months, the plug is surgically accessed and removed. The distance between the two bores is then measured and a bar made of suitable biocompatible material is cut and each end inserted into a transversely extending bore formed in the head portion of a bar attachment abutment member. The bar attachment abutment members, also made of suitable biocompatible material, each has a post portion having a selected locking taper adapted to be lockably received in a repective bore of a root implant member with the transversely extending bore extending at a right angle to the longitudinal axis of the post portion. The post portions of the first and second bar attachment abutment members with the bar extending therebetween, are then inserted into the respective first and second bores of the root implant members and tapped in to lock the post portions therein. If desired, a bar attacment abutment member can be formed with a second bore adapted to receive another bar extending to another bar attachment abutment member in a third root member.

According to a feature of the invention the transversely extending bore in the head portion of the bar attachment abutment may be formed with a taper to allow for a slight degree of misalignment, either in depth and/or in parallelism.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings.

DETAILED DESCRIPTION OF PREFERRED EMBODIMENTS

Figure 1:
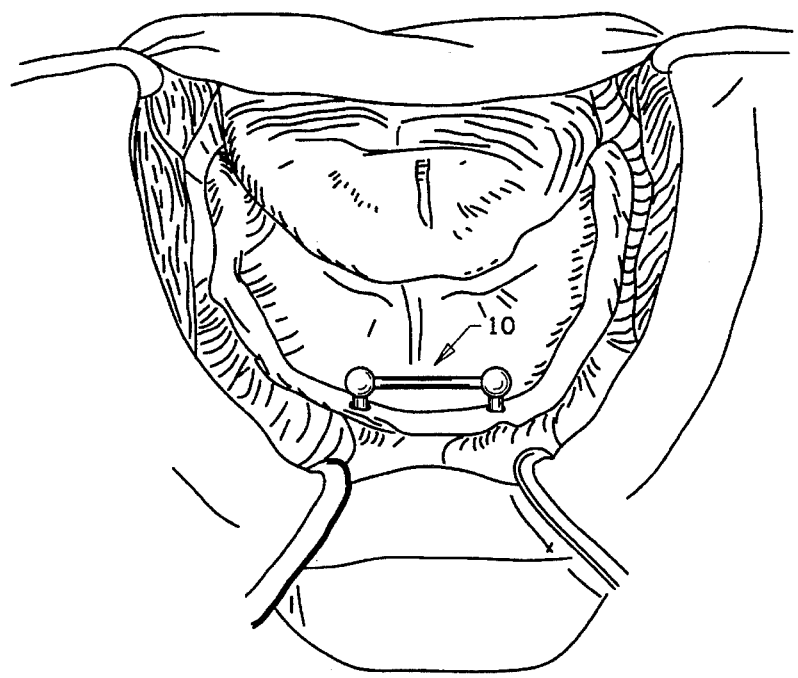
FIG. 1 is a perspective view of a patient's mouth in which an overdenture bar assembly made in accordance with the invention has been placed.
Figure 2:
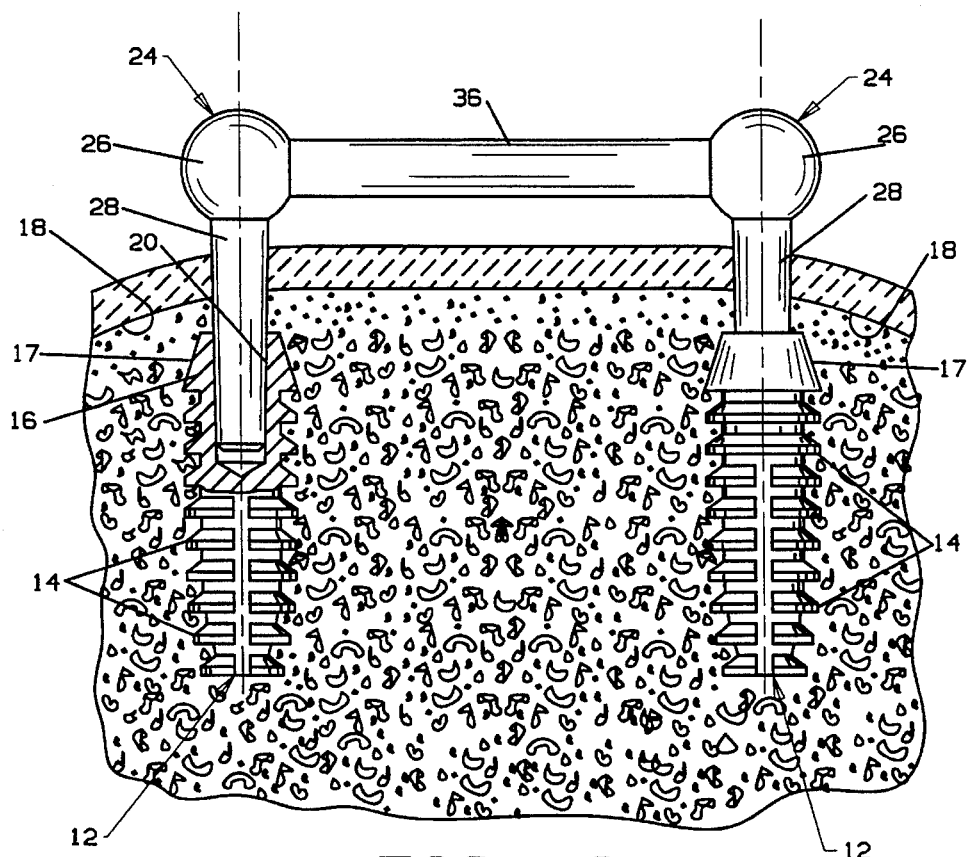
FIG. 2 is a vertical sectional view along the alveolar ridge showing an overdenture bar assembly made in accordance with the invention in place in a patient's mouth, a portion of one of the two implant members shown being in cross-section.

With regard to FIGS. 1 and 2, an overdenture bar assembly 10 comprises first and second root members 12 formed of suitable biocompatible material such as commercially pure titanium or a titanium alloy, e.g., a titanium-aluminum-vanadium alloy. Each of root members 12 has a plurality of outwardly extending fins 14 and, in the direction going toward the crestal end, a shoulder 16 having a taper 17 of decreasing diameter. Root member 12 is positioned within a socket formed in the alveolar ridge so that its upper surface, as seen in FIG. 2, or the end surface closest to the crest 18 of the bone, is slightly below the crest 18, e.g., approximately 2 mm.

An upwardly opening, post-receiving bore 20 is formed in the root member through the crestal or top end surface 22 having a locking taper relative to that of a post to be received therein.

Root members 12 are of the type shown in U.S. Pat. No. 4,738,623, the subject matter of which is incorporated herein by this reference and to which reference may be had for further details.

Figure 3:
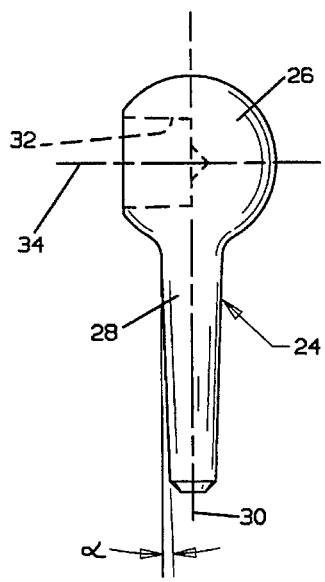
FIG. 3 is a front elevation of a bar attachment abutment member used in the FIGS. 1, 2 assembly.
Figure 4:
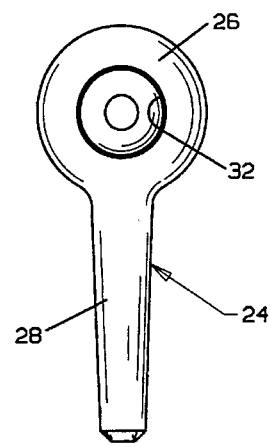
FIG. 4 is a side elevation of the FIG. 3 abutment member.
Figure 5:
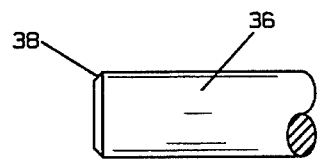
FIG. 5 is a front view of a portion of a bar used in the FIGS. 1, 2 assembly.

First and second bar attachment abutments members 24 each comprise a head portion 26, preferably having a smooth rounded surface such as a spherical configuration to minimize irritation of tissue and the formation of occlusions and the like and a post portion 28 extending therefrom. A cross-section of post portion 28 taken vertically relative to the longitudinal axis 30, FIG. 3, is circular and the post portion is formed with a taper of decreasing diameter going in a direction away from the head portion 26. The taper is selected relative to the taper of bore 20 to be a locking taper, e.g., within approximately 3 degrees. In post portions made in accordance with the invention a taper of 1 degree and 24–32 minutes has been found to be very effective. A transversely extending bore 32 (FIGS. 3, 4) is formed in head portion 26 having a longitudinal axis 34 extending perpendicular to that of axis 30. The depth of the bore is selected to be sufficient to securely seat a cylindrical bar to be described below, preferably extending approximately to longitudinal axis 30.

A cylindrical bar 36 formed of suitable biocompatible material, preferably the same as that of abutment members 24, having a diameter selected so that it can be closely slipped into transversely extending bore 32 has a respective end received in bore 32 of each abutment member 24. Preferably a chamfer 38 is formed at each end of the bar to facilitate insertion into bore 32.

Figure 6:
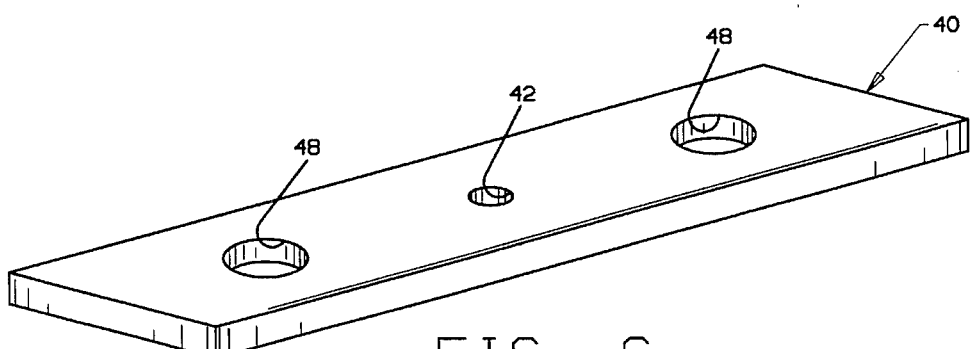
FIG. 6 is a perspective view of a parallelism/depth jig used in implanting the root members.
Figure 7:
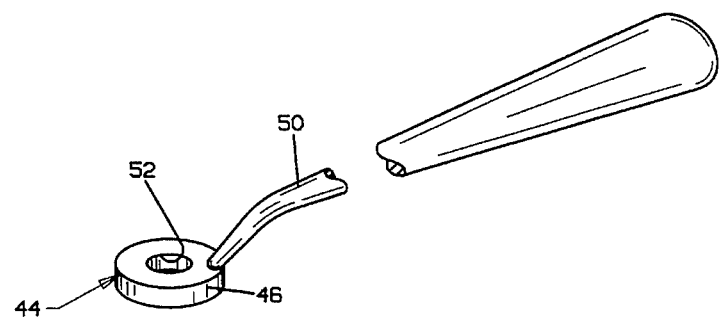
FIG. 7 is a perspective view of an insert used with the FIG. 6 jig.

In using the bar overdenture system the restorative dentist initially exposes the front of the jaw bone and, in effect forms a shelf there. A reference bore is drilled generally centrally in the shelf and a pin is then placed in the reference bore. The jig member 40, FIG. 6, a generally flat plate having a central reference bore 42 between two outer bores 48, is placed on the shelf with the pin received in a reference bore 42 which closely matches the diameter of the pin. Insert member 44, FIG. 7, comprising an annular base 46, has an outer diameter closely matching that of outer bores 48 and, using handle 50, is inserted in each of outer bores 48. Preferably, two or more inserts 44 are used with different internal diameter bores 52, e.g., 2 mm, 3 mm, in outer bores 48 of 4 mm diameter so that a small pilot hole can be first drilled and then its size increased by using an insert with a progressively larger bore and then finally using bore 48 without an insert. Each drill bit is marked at an appropriate axial distance from the end of the drill bit so that when the mark comes into registration with the top surface of jig member 40 or insert 44 the proper depth of the bore in the bone of the jaw has been achieved. The thickness of the plate of jig 40 and insert 44 is sufficient, along with the close fit of a bur or drill bit into a repective bore of the jig, to provide parallelism of the drilled bores.

The dentist implants a root member in each socket with the longitudinal axes of the post receiving bores parallel with one another as described above. The root members are packed with autogenous material, preferably harvested while drilling the bores in the bone, and the mucoperiosteal flaps are closed over the root members and healing plugs received in bores 20 of the root members, sutured and allowed to heal, generally for three months or more.

After sufficient healing has occurred the healing plugs are surgically accessed and removed. The distance between the closed ends of the two bores is measured and a bar 36 is cut to that measurement. Preferably, to avoid the possibility of undesirable lateral stress placed on the alveolar bone the length of bar 36 is selected to be just under the measured distance, e.g., approximately 1 mm less than the measured distance. Preferably, a slight chamfer 38 is formed in each end of bar 36 to facilitate insertion into transversely extending bore 32. Each end of the rod is then inserted into transversely extending bore 32 of a respective bar attachment abutment member and held together while the bar attachment abutment members are tapped into the root members locking them in place.

It will be appreciated that, if desired, the measurement between the sockets in the bone can be taken at the time the root members are implanted and the bar prepared in the interim so that it is ready for installation at the time the patient returns to have the healing plugs replaced with the bar attachment abutment members.

Transversely extending bores 32 of bar attachment abutment members 24 are preferably formed with a slight taper with the diameter of the bore decreasing going in the direction into the bore, e.g., 1.5 degrees, to accommodate a certain amount of misalignment. For example with a bar 36 of 22 mm in length and a diameter 0.0787/0.0777 and a bore 32 of 0.0807/0.0797 misalignment of 1 degree 45 minutes is accommodated.

A suitable jig member 40 made in accordance with the invention has a length of 26 mm, a width of 7 mm and a thickness of 2 mm. The center reference bore has a diameter of 2 mm and the outer bores each have a diameter of 4 mm. Inserts 44 have an outer diameter of 4 mm, a thickness of 2 mm and inside diameters of 2 and 3 mm.

As noted above, a single measurement is made to cut the bar to the proper length and the two abutment members and the bar are inserted into the implanted root members without any concern of the prior art problem of timing, or angular position of a threaded member relative to the axial position of the member. This chairside procedure completely obviates the need for laboratory involvement and concomitant expense as well as reducing the number of office visits by the patient by as much as four for most dentists. Although the combination of root members and bar attachment abutment members each having a locking taper is particularly advantageous, it is within the purview of the invention to use other types of root members and abutments, such as those having threaded attachment means, as long as bar attachment members are provided with posts having a locking taper receivable in a matching bore in an implant means so that the bar can be inserted into transversely extending bores in the bar attachment members with the posts automatically properly angularly positioned to be received in the matching bores of the implant means.

Although the invention has been described with regard to a specific preferred embodiment thereof, variations and modifications will become apparent to those skilled in the art. It is therefore the intention that the appended claims be interpreted as broadly as possible in view of the prior art and to include all such variations and modifications.

What is claimed:

1. An overdenture bar assembly comprising first and second implant means, each having a tapered circular bore having a longitudinal axis, first and second bar attachment members each having a head portion and a tapered post portion having a longitudinal axis extending from the head portion, a cross-section of the post portion taken perpendicular to the longitudinal axis of the post portion being circular, the taper of the post portion selected relative to the taper of the bore to form a locking joint, the head portion of each bar attachment member formed with a transversely extending bore having a longitudinal axis generally perpendicular to the longitudinal axis of the respective post portion, and a bar having an outer periphery selected to be closely received in the transversely extending bore of each head portion, the bar having opposite ends, each end received in a respective transversely extending bore with the post portions each received in a respective implant means.

2. The overdenture bar assembly according to claim 1 in which each head portion is formed with a smooth curved outer surface.

3. The overdenture bar assembly according to claim 2 in which at least a portion of each head portion has a spherical outer surface.

4. The overdenture bar assembly according to claim 1 in which the transversely extending bore in the head portion of each bar attachment member is generally cylindrical having a taper to accommodate a slight misalignment.

5. The overdenture bar assembly according to claim 4 in which the taper in the transversely extending bore in the head portion is approximately 1.5 degrees.

6. The overdenture bar assembly according to claim 1 in which the implant means, bar attachment members and bar are formed of a titanium alloy.

7. The overdenture bar assembly according of claim 1 in which the transversely extending bore extends to the longitudinal axis of the respective post portion.

8. The overdenture bar assembly of claim 1 in which each implant means comprises a root member having a crestal end in which the tapered circular bore of the implant means is formed through the crestal end.

9. A method for mounting an overdenture bar assembly in the maxillary or mandibular alveolar bone of a patient comprising the steps of forming first and second root member receiving sockets in the bone, positioning a root member in each socket, the root members each having a longitudinal axis and a crestal end and having a tapered bore formed in the root member through the crestal end, taking first and second abutment members each having a head portion and a post portion extending from the head portion, the post portion having a longitudinal axis and having a taper selected relative to the taper of the bore in the root members to form a locking engagement when the post portion is tapped into the bore of the root member, the head portion having a transversely extending bore with a longitudinal axis essentially perpendicular to the longitudinal axis of the post portion and having a selected depth, taking an elongated, generally cylindrical bar having a diameter selected so that it closely fits into the bore in each head portion and cutting the bar generally to the length between the longitudinal axes of the first and second root members compensated by the selected depth of the transversely extending bores, inserting each end of the bar into the transversely extending bore in the head portion of a respective abutment member, holding the bar and abutment members together while inserting the post portions into the bores of respective root members and tapping the abutment members into locking engagement with the root members.

10. A method according to claim 9 in which the transvesely extending bore in each head portion extends essentially to the longitudinal axis of the repective post portion and the measured length of the bar is slightly less than the distance between the longitudinal axes of the first and second root members.

11. A method according to claim 9 including the step of forming a taper in the transversely extending bore of each head portion to accommodate a selected amount of misalignment.

12. A method according to claim 9 in which parallelism is obtained for the first and second root member receiving sockets by, prior to forming the first and second root member receiving sockets, forming a shelf surface on the alveolar bone of the patient and forming a reference bore in the bone, inserting a pin in the reference bore, placing a plate on the shelf surface, the plate having a center bore closely fitting the pin between first and second outer bores and directing a drill bit into each outer bore to form the first and second root member receiving sockets, the drill bit having an outer surface closely matching that of the outer bores so that the thickness of the plate serves to guide the drill bit.

13. A method according to claim 12 in which annular inserts closely fitting the outer bores are provided having selected inside diameter bores so that a pilot bore can be initially formed at the location of the first and second root member receiving sockets and then enlarged by selecting inserts with progressively larger inside diameter bores.

14. Apparatus for facilitating the forming of first and second root member receiving sockets in the alveolar bone of a patient comprising a generally flat plate member having a central reference bore disposed between first and second outer bores, the outer bores each having essentially identical diameters, and annular insert members closely receivable in the outer bores, the insert members having a bore selected to provide a guide surface for a drill bit received therethrough and an elongated handle attached to each insert member and extending therefrom to facilitate insertion and removal of the insert members into and out of a respective outer bore.

15. Apparatus according to claim 14 in which the thickness of the plate member and insert members is at least approximately 2 mm.

* * * * *